(12) United States Patent
Loritz

(10) Patent No.: US 10,478,567 B2
(45) Date of Patent: Nov. 19, 2019

(54) CHILD RESISTANT SYRINGE

(71) Applicant: Kenneth Anthony Loritz, Irvine, CA (US)

(72) Inventor: Kenneth Anthony Loritz, Irvine, CA (US)

(*) Notice: Subject to any disclaimer, the term of this patent is extended or adjusted under 35 U.S.C. 154(b) by 229 days.

(21) Appl. No.: 15/526,082

(22) PCT Filed: Nov. 11, 2015

(86) PCT No.: PCT/US2015/060177
§ 371 (c)(1),
(2) Date: May 11, 2017

(87) PCT Pub. No.: WO2016/077470
PCT Pub. Date: May 19, 2016

(65) Prior Publication Data
US 2018/0353701 A1    Dec. 13, 2018

Related U.S. Application Data

(60) Provisional application No. 62/078,133, filed on Nov. 11, 2014.

(51) Int. Cl.
*A61M 5/32*  (2006.01)
*A61M 5/00*  (2006.01)

(52) U.S. Cl.
CPC .......... *A61M 5/3202* (2013.01); *A61M 5/002* (2013.01); *A45D 2200/055* (2013.01); *A61M 2209/06* (2013.01)

(58) Field of Classification Search
CPC ........... A61M 5/002; A61M 5/3202; A61M 2209/06; A61M 35/00; A61M 35/003
See application file for complete search history.

(56) References Cited

U.S. PATENT DOCUMENTS

| 945,118 | A | * | 1/1910 | Campbell | |
| 3,008,570 | A | * | 11/1961 | Roehr | A61M 5/002 206/229 |
| 3,094,130 | A | * | 6/1963 | Wiener | A46B 11/0017 222/394 |
| 3,685,514 | A | * | 8/1972 | Cheney | A61M 5/31596 604/90 |

(Continued)

FOREIGN PATENT DOCUMENTS

WO  WO 2012/069969 A1  5/2002
WO  WO 2014/001880 A1  1/2014

OTHER PUBLICATIONS

PCT/US2015/060177, International Search Report and Written Opinion, dated May 12, 2016.

*Primary Examiner* — Laura A Bouchelle
(74) *Attorney, Agent, or Firm* — Fay Sharpe LLP

(57) ABSTRACT

A syringe assembly includes a housing having a cavity for receiving an associated fluid. A plunger assembly includes a piston and a shaft connected thereto for selectively dispensing the associated fluid from the housing through a dispensing opening. A container receives the housing and plunger assembly. The container has a first opening at a first end that selectively receives a cap thereon and covers the dispensing opening when the cap is secured to the container, and second opening at a second end that opens to the plunger assembly shaft.

14 Claims, 24 Drawing Sheets

(56) References Cited

U.S. PATENT DOCUMENTS

| | | | | |
|---|---|---|---|---|
| 3,807,881 A | * | 4/1974 | Seidler | A45D 40/26 |
| | | | | 401/175 |
| 4,277,194 A | * | 7/1981 | Smith | A46B 11/0027 |
| | | | | 222/326 |
| 4,300,678 A | * | 11/1981 | Gyure | A61M 5/002 |
| | | | | 206/364 |
| 4,874,385 A | | 10/1989 | Moran et al. | |
| 5,344,405 A | * | 9/1994 | Richards | A61M 5/326 |
| | | | | 604/110 |
| 5,842,487 A | * | 12/1998 | Ledet | A46B 11/0027 |
| | | | | 132/308 |
| 7,874,426 B2 | * | 1/2011 | Castellani | A61M 5/002 |
| | | | | 206/364 |
| 8,641,661 B2 | | 2/2014 | Delmotte | |
| 2005/0036823 A1 | * | 2/2005 | Butcher | A45D 34/04 |
| | | | | 401/266 |
| 2010/0168678 A1 | | 7/2010 | Glocker | |
| 2013/0043282 A1 | | 2/2013 | Niklasson | |
| 2014/0288506 A1 | | 9/2014 | Mumford et al. | |

* cited by examiner

CHILD RESISTANT SYRINGE

The present application claims the priority benefit of U.S. provisional application Ser. No. 62/078,133, filed Nov. 11, 2014, the disclosure of which is incorporated herein in its entirety.

BACKGROUND

The present disclosure relates to a dispensing apparatus, and particularly to an apparatus that dispenses a fluid-like substance (e.g., oil, perfume, liquid medicines, etc.). It is often desirable to dispense a small amount of a fluid-like substance in a controlled manner. One convenient way of dispensing such a substance is through use of a syringe. The container or syringe housing forms a cavity that receives the substance. A first end of the syringe housing has a small opening through which the substance is dispensed. A plunger or plunger assembly has a piston adjacent a first end thereof where the piston sealingly engages an inner surface of the housing as the piston slides in the cavity. The plunger also includes a shaft that extends axially outward from the syringe housing, for example, at an end opposite that of the small dispensing opening. It is intended that the shaft be engaged (finger, thumb) by a user at an outer, terminal end of the shaft to depress the piston, i.e., move the piston through the cavity, and thereby discharge fluid through the syringe opening in a manner well known in the art. Oftentimes a needle or other dispensing head can be selectively mounted on and selectively removed from the syringe housing dispensing opening. When removed, it would also be desirable to be able to store the needle or dispensing head for easy access when the user would like to re-mount the dispensing head on the syringe housing dispensing opening.

In certain instances, it would also be desirable to prevent tampering with the contents of the syringe housing, for example, by children. It would be desirable that access to the substance contained in the syringe housing be limited through use of a child-resistant threaded cap for the container, e.g., one that requires simultaneous actions on the cap to remove the cap from the container such as depressing and rotating, squeezing and rotating, etc.

Related tampering issues include apprising the user whether the contents of the syringe housing have been previously exposed or to prevent a user from subsequently recharging the syringe housing once the fluid contents have been dispensed therefrom. That is, there may be a desire to have the contents of the syringe housing dispensed only once. In those situations, therefore, once the plunger assembly is depressed and the fluid contents emptied from the syringe housing, the user cannot refill the housing with additional fluid.

Still another desired feature is to seal the fluid contents of the syringe housing between uses.

It would also be desirable to monitor an amount of fluid remaining in the syringe housing, particularly when adding other features to the assembly makes it difficult to view the amount of fluid remaining in the syringe housing to be dispensed, or evaluate view the amount of fluid that has been dispensed.

Still another desirable feature would be the ability to easily store the needle or dispensing head in a convenient fashion with the syringe assembly.

Accordingly, a need exists for one or more of these features to be added to a syringe assembly.

SUMMARY

A syringe assembly includes a housing having a cavity for receiving an associated fluid therein and having a dispensing opening communicating with the cavity through which the associated fluid is selectively dispensed. A plunger assembly is connected to the housing and includes a piston and a shaft connected to the piston for selectively dispensing the associated fluid from the housing dispensing opening. A container receives the housing and plunger assembly. The container has a first opening at a first end that selectively receives a cap thereon and covers the dispensing opening when the cap is secured to the container, and a second opening at a second end that opens to the plunger assembly shaft.

In one embodiment, at least a portion of the shaft extends through the container second opening, while in another embodiment the shaft is dimensioned so that it does not extend through the container second opening.

The shaft includes a stop member that selectively engages a surface of the container to limit movement of the shaft.

A storage compartment may be provided in the container for selectively storing associated tools therein.

A topical applicator is mounted to the container and communicates with the dispensing opening.

A helical drive assembly is operatively associated with the shaft for advancing and retracting the shaft relative to the housing.

In one embodiment, the helical drive assembly includes a helical thread on a portion of the shaft that cooperates with a corresponding helical surface on the container to rotationally and axially advance and retract the shaft relative to the housing.

In another embodiment, the helical drive assembly includes cooperating first and second shaft portions that each include a helical thread region such that rotation of the first shaft portion results in advancement of the second shaft portion relative to the housing for selectively dispensing the associated fluid.

An indicator member is visible through the container to represent an amount of the associated fluid used or remaining in the housing cavity.

Indicia on the container are provided adjacent the indicator member.

A seal is provided for selectively closing the dispensing opening.

In one embodiment, the seal is a foil member that is received over the dispensing opening. In another embodiment, the seal has a protrusion dimensioned for frictional engagement with the dispensing opening. In yet another embodiment, the dispensing opening is located at the first end of the container for sealing engagement with an underside of the cap when the cap is secured to the container.

One advantage of the present disclosure is the ability to enclose the syringe assembly in a container that can be selectively opened and closed.

Another benefit resides in the ability to modify an existing container (jar) by forming an opening in a second end to allow access to a shaft of the plunger assembly of the syringe assembly. In one version, the shaft extends through the opening while in another, the shaft can only be depressed through the opening.

A stop member may be provided in the shaft to limit re-filling of the syringe cavity.

An indicator disk is provided to illustrate the amount of fluid remaining in the syringe assembly or that has been used.

A storage compartment can be easily incorporated into the syringe assembly.

Still another advantage is the ability to easily seal the dispensing opening of the syringe, either to evidence tampering, or to prevent the fluid held in the housing cavity will be exposed to atmosphere.

Still other benefits and advantages of the present disclosure will become more apparent from reading and understanding the following detailed description.

DETAILED DESCRIPTION

Figure 1:
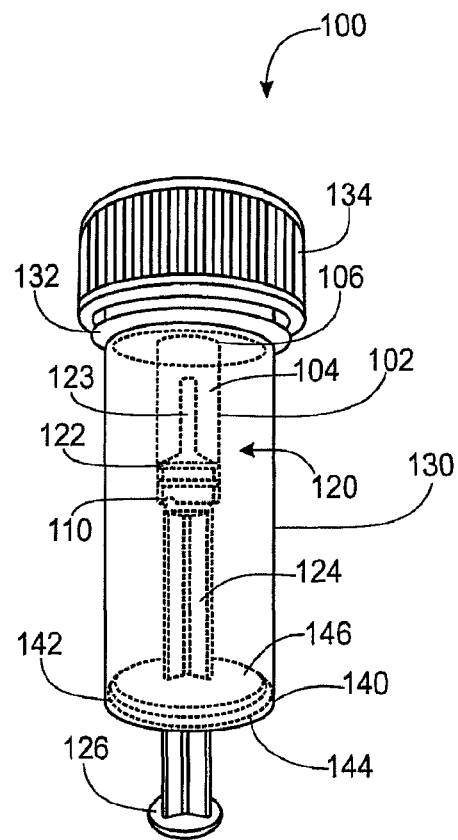
FIG. 1 is an elevational view of a preferred embodiment of a child resistant syringe assembly.
Figure 2:
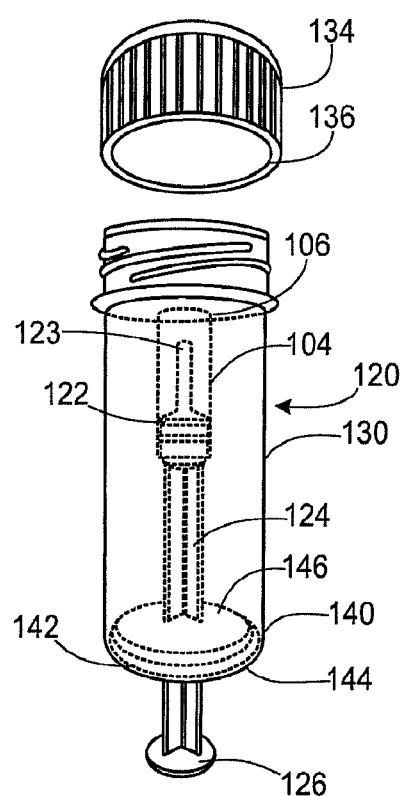
FIG. 2 is an elevational view similar to FIG. 1 with the cap removed from the assembly.
Figure 3:
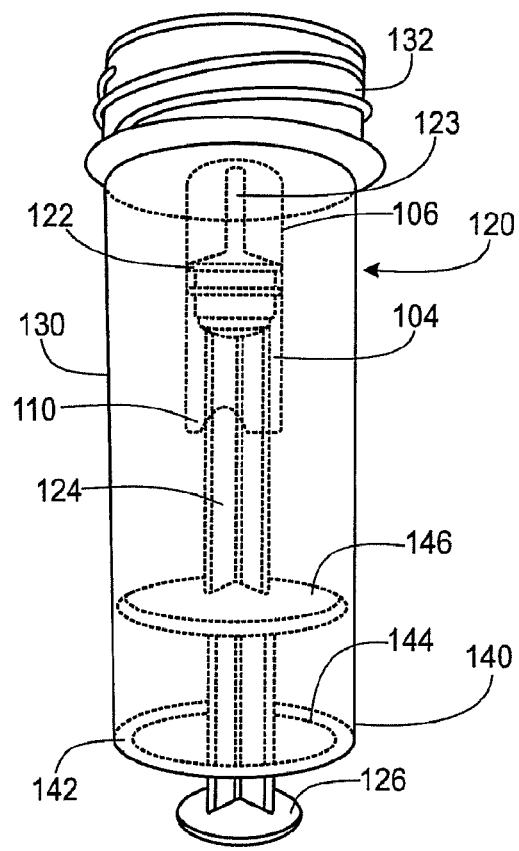
FIG. 3 is an elevational view similar to FIG. 2 with the plunger partially depressed.
Figure 4:
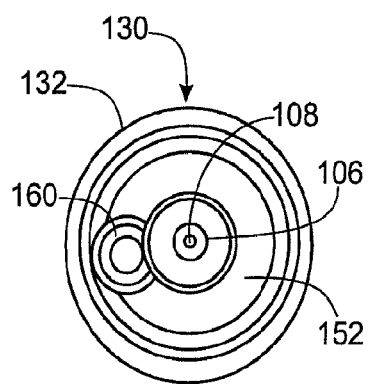
FIG. 4 is a top plan view of the syringe assembly of FIG. 3 with the cap removed from the assembly.
Figure 5:
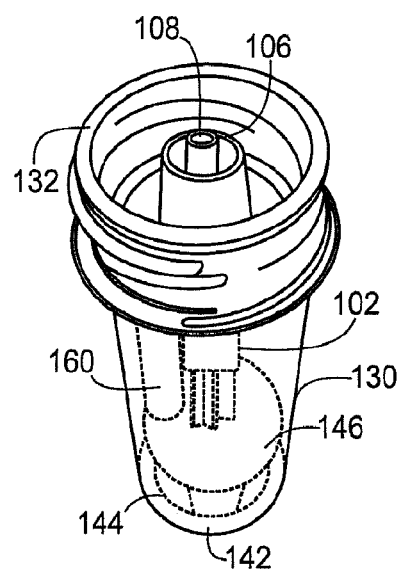
FIG. 5 is a perspective view of the syringe assembly of FIG. 3 with the cap removed.
Figure 6:
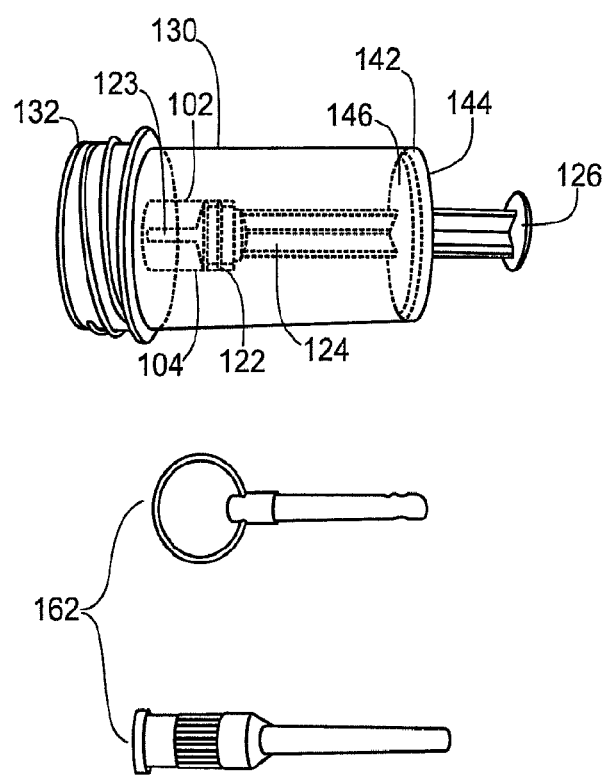
FIG. 6 shows other tools/components that may be provided with the child resistant syringe assembly.
Figure 7:
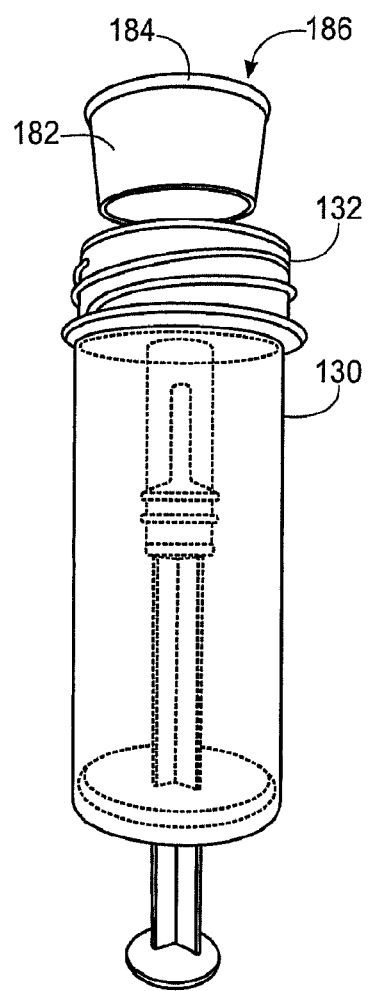
FIG. 7 is an elevational view of a modified syringe assembly that incorporates a spreader/topical applicator head.
Figure 8:
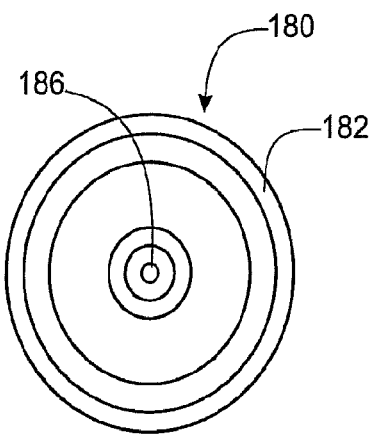
FIG. 8 is a plan view of an underside of the spreader/topical applicator head.
Figure 9:
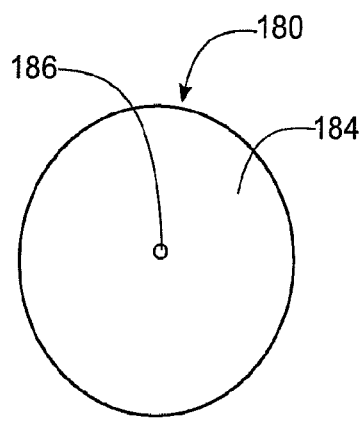
FIG. 9 is a plan view of the top side of the spreader/topical applicator head.
Figure 10:
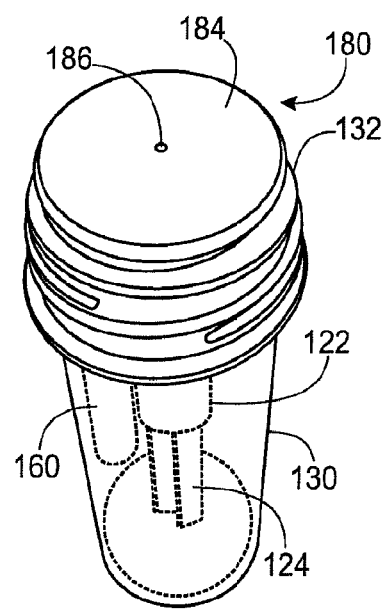
FIG. 10 is a perspective view of the spreader/topical applicator head installed on the modified syringe assembly.
Figure 11:
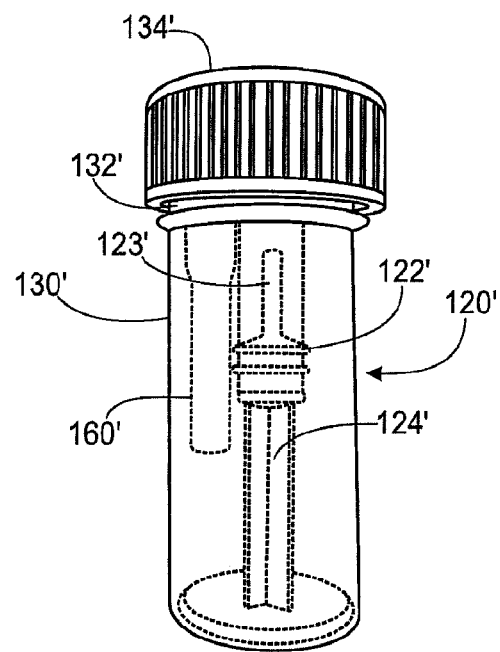
FIG. 11 is an elevational view of another preferred embodiment of a child resistant syringe assembly.
Figure 12:
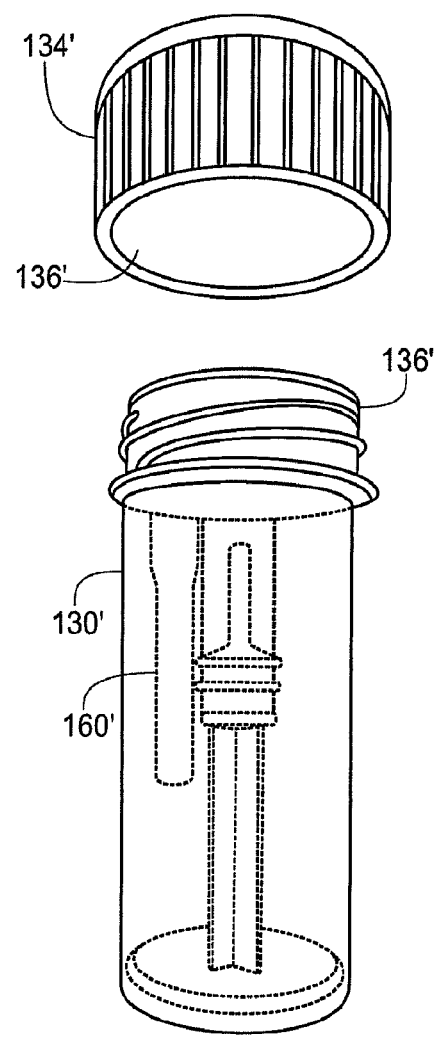
FIG. 12 is an elevational view of the embodiment of FIG. 11 with the cap removed.
Figure 13:
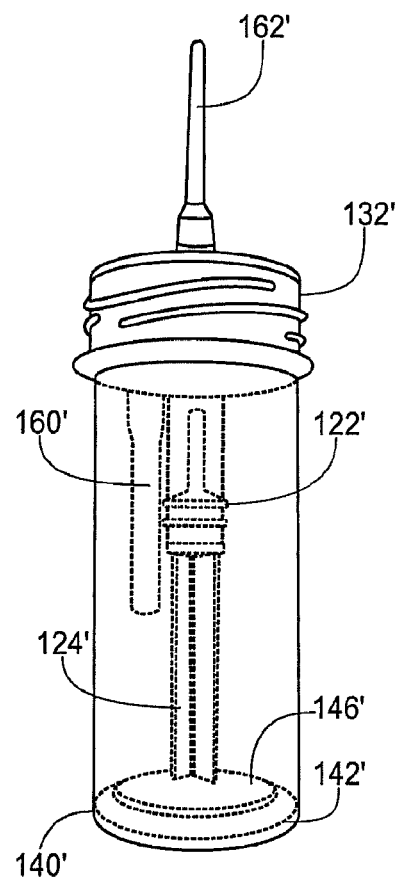
FIG. 13 is an elevational view of the embodiment of FIG. 11 with the cap removed, a dispensing head installed thereon, and the plunger assembly partially depressed.
Figure 14:
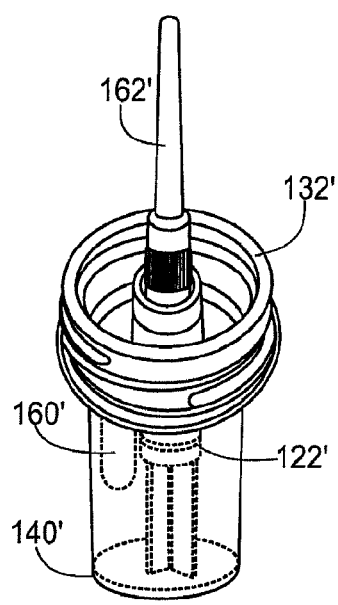
FIG. 14 is a perspective view of the embodiment of FIG. 11 with the dispensing head installed thereon.
Figure 15:
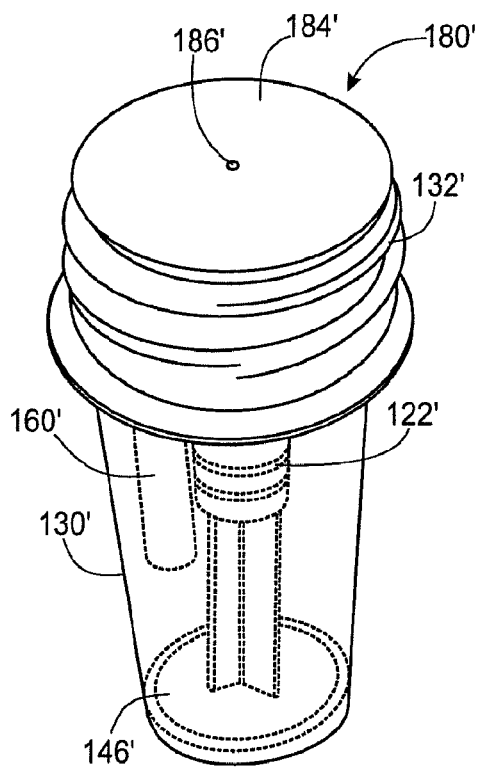
FIG. 15 is a perspective view of the embodiment of FIG. 11 with a spreader/topical applicator head installed on the syringe assembly.
Figure 16:
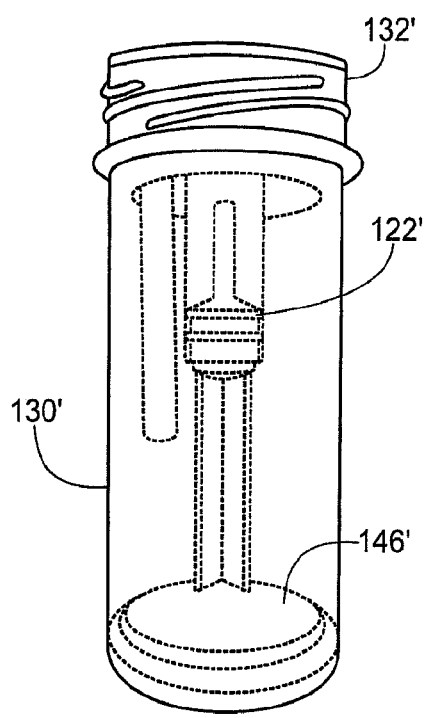
FIG. 16 is an elevational view of the embodiment of FIG. 11 with the dispensing head removed.
Figure 17:
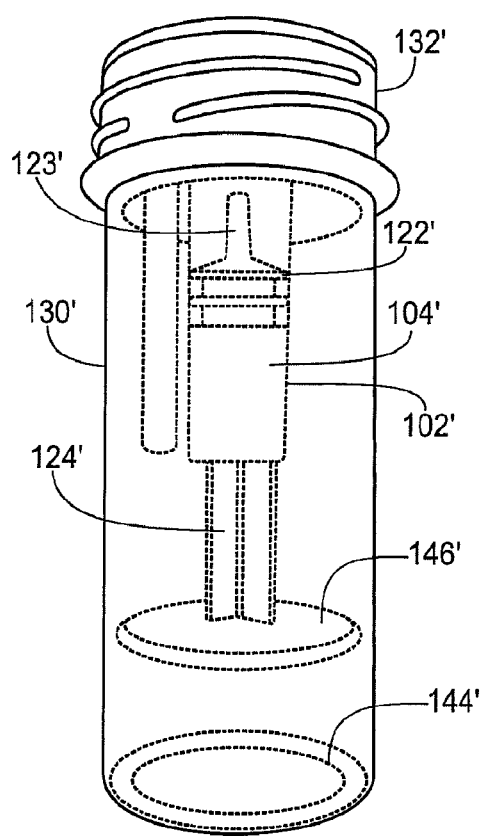
FIG. 17 is an elevational view similar to FIG. 16 with the plunger assembly partially depressed.
Figure 18:
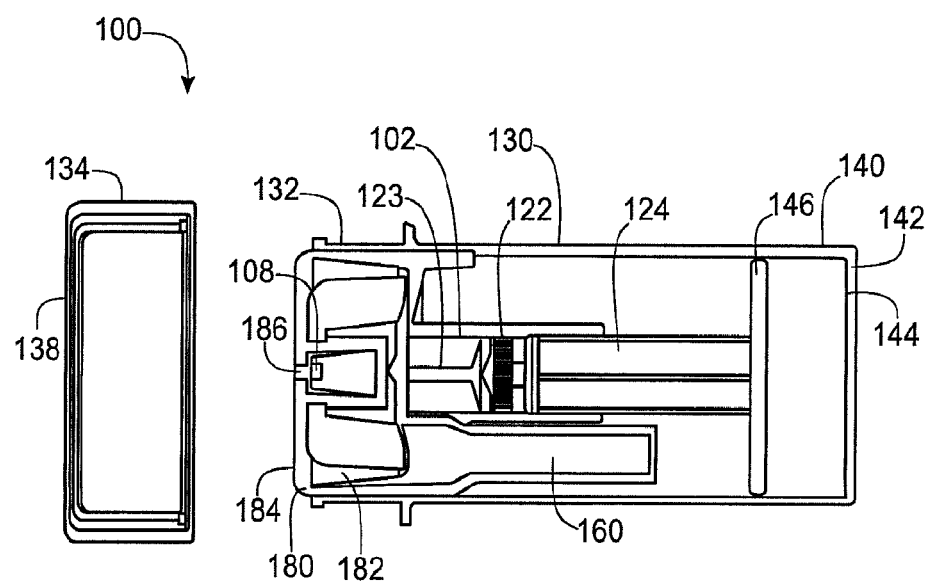
FIG. 18 is an elevational view shown partially in cross-section of the embodiment of FIG. 11 with the cap shown in an open position.
Figure 19:
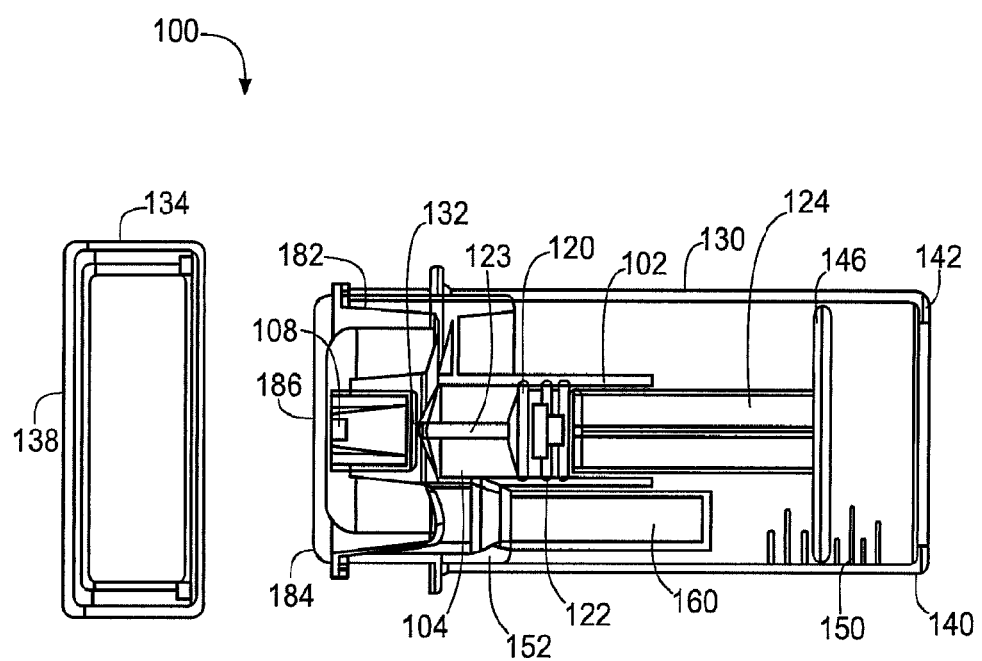
FIG. 19 is a cross-sectional view of the embodiment of FIG. 11 with the cap shown in an open position and the plunger assembly partially depressed.
Figure 20:
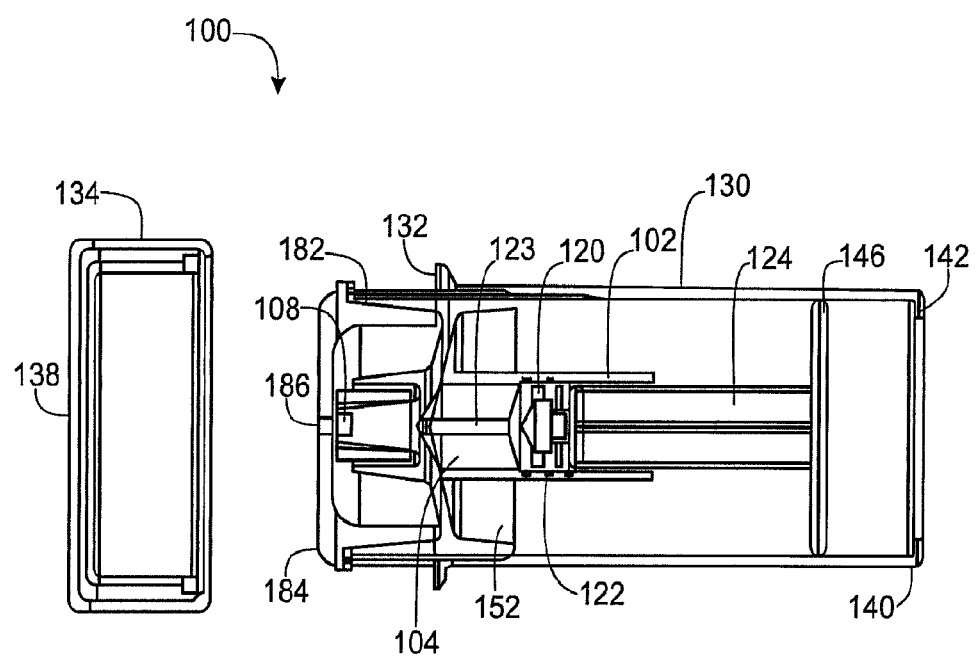
FIG. 20 is a cross-sectional view of the embodiment of FIG. 11 similar to FIG. 19 but rotated through 90°.

Turning first to FIGS. 1-6, there is shown a syringe assembly 100 that includes a hollow body or syringe housing 102 that encloses a cavity 104. The housing 102 has a first end 106 with a small opening 108 (FIGS. 4-5) for selectively dispensing a fluid product (not shown) that is stored in the cavity 104 of the housing. A second end 110 of the housing 102 receives a plunger assembly 120. The plunger assembly includes a plunger or piston 122 that is dimensioned to slidably and sealingly engage an inner surface of the housing 102. For example, the piston 122 can be formed at least in part from a material (for example an elastomeric or plastic material) that is easily deformed and provides the sliding, sealing interface around an outer periphery of the piston with the inner surface of the housing 102. In addition, a plunger gasket tip extension 123 may be protrude outwardly from the piston 122 to facilitate dispensing of the fluid from the cavity 104 and eliminate waste that a typical syringe leaves in the enlongated long tip of the syringe.

A shaft 124 extends outwardly from one side of the piston 122. The shaft 124 is dimensioned to extend axially from the second end 110 of the housing 102. In the embodiment of FIGS. 1-6, a terminal end of the shaft 124 preferably includes a surface such as flat surface 126 dimensioned for engagement with a finger of a user to selectively advance the plunger assembly 120 relative to the housing 102 whereby the piston 122 pushes/dispenses the fluid from the housing cavity 104 through the small opening 108 in the first end 106 of the housing.

The child resistant syringe assembly 100 also includes a surrounding container or jar 130. As shown in this embodiment, the container 130 has a generally cylindrical conformation in which a first, upper end 132 receives the syringe housing 102 therein. Preferably, an outer surface of the first end 132 of the container 130 is threaded to operatively receive a cap 134 having internal threads 136. The first end 106 of the syringe housing 102 is essentially flush or may extend slightly outward from the container 130 for selective sealing engagement with a substantially planar, inner surface 138 of the cap 134 when the cap is closed on the container. Locating the dispensing opening 108 of the syringe assembly so that it is substantially flush with the top of the container 130 advantageously makes more difficult for a child to suck on the end of the syringe. This is in contrast to a standard everyday syringe (not shown) designed to readily dispense liquid cold medicines, for example, so that children can take the medication orally from the end of the syringe. In addition, when the cap 134 is threaded onto the container 130, the fluid contained in the syringe housing 102 is sealed from the external environment due to the sealing engagement of the terminal end of the syringe housing with the inner surface 138 of the cap.

The cap 134 is preferably a child resistant construction that requires depression (or compression of the sidewall) of the cap while simultaneously rotating the cap relative to the container 130. These structural and functional details of such a child resistant cap and container are well known to those skilled in the art so that further description herein is deemed unnecessary to a full and complete understanding of the present disclosure.

A second end 140 of the container 130 has a bottom wall 142 with an opening 144 dimensioned to allow the shaft 124 to extend outwardly from the container. The bottom wall 142 extends radially inward toward the shaft 124 and forms or serves as a stop surface that selectively engages a stop member/indicating disk 146 mounted to an intermediate portion of the shaft. In this manner, when the shaft 124 is fully retracted relative to the syringe housing 102, the stop member 146 abuts against the bottom wall 142 of the container 130. This arrangement of the disk 146 and bottom wall 142 prevents inadvertent removal of the plunger assembly 120 from the syringe housing 102. In addition, the stop member 146 operates as an indicating disk in conjunction with indicia 150 (e.g. calibrated lines formed on the container 130) to provide a representation of the location of the piston assembly 120 relative to the syringe housing 102.

Further, the syringe housing 102 cooperates with a holding portion 152 that abuts against the inner wall of the container 130 at the upper, first end 132 thereof. In one preferred arrangement, the holding portion 152 is integrally formed with the syringe housing 102 and securely locates the syringe housing relative to the surrounding container 130, although it is also contemplated that the holding portion/syringe housing can be made separately from the container 130 and subsequently joined thereto. The holding portion 152 may also include a storage compartment 160 extending axially inward in generally parallel arrangement with the syringe housing 102 and also received in the container 130. The storage compartment 160 is dimensioned to receive a removable dispensing head or other tools 162, for example (see FIG. 6). A more complete description and understanding of the storage compartment may be found in commonly owned, published international patent application WO2015/123546, international filing date Feb. 13, 2015. The storage compartment 160 may be selectively accessed when the cap 134 is removed from the container 130. When sharps (blunt needles and hypodermic needles) are removed from the luer tip, they can be safely placed into the luer tip insert storage compartment 160 for safe sharps disposal.

Still another feature of the present disclosure is the inclusion of a topical applicator or spreader head 180 (see FIGS. 7-10). The applicator head 180 may be mounted to the container 130, syringe housing 102, holding portion 152, or therebetween, via a friction fit of annular sidewall 182 with the container, syringe housing and/or holding portion. The applicator head 180 has an end surface 184 with an opening 186 that generally aligns with the dispensing opening 108 in the syringe housing. Thus, installation of the applicator head 180 on the container 130 allows fluid dispensed from the opening 108 in the syringe housing to pass through the opening 186 of the applicator head and be quickly and smoothly distributed over the end surface 184 for a topical application over a wide surface area.

Another embodiment is illustrated in FIGS. 11-20. Many of the same structural components and functional features as described in connection with the earlier embodiments of FIGS. 1-6 and 7-10 are incorporated into the arrangement shown in FIGS. 11-20. For purposes of brevity and ease of understanding, like components will be referenced by like reference numbers with a primed suffix (') (e.g., container 130 in FIGS. 1-10 now shown and referenced as container 130' in FIGS. 11-20) and new elements will be identified by new reference numerals. The primary distinction is the fact that the shaft 124' does not extend outwardly from the container 130'. Stop member/indicating disk 146' is mounted to the shaft 124' but instead forms a terminal end of the shaft so that the entire shaft is surrounded by the container 130' even when the shaft is fully extended. In this manner, when the shaft 124' is fully extended relative to the syringe housing 102', the stop member 146' abuts against the bottom wall 142' of the container 130'. This stop arrangement prevents inadvertent removal of the plunger assembly 120 from the syringe housing 102' and also provides for one-time use of the syringe assembly 100' since a user cannot access the plunger assembly 120' when extended/retracted relative to the syringe housing 102' to refill the cavity 104'. The stop member 146' still operates as an indicating disk in conjunction with the calibrated lines or indicia 150' formed on the container 130' (see FIG. 19) and thereby provide a representation of the location of the piston assembly 120' relative to the syringe housing 102'. This provides an easy indication of the amount of fluid used or fluid remaining in the cavity 104' of the syringe housing 102'.

Figure 21:
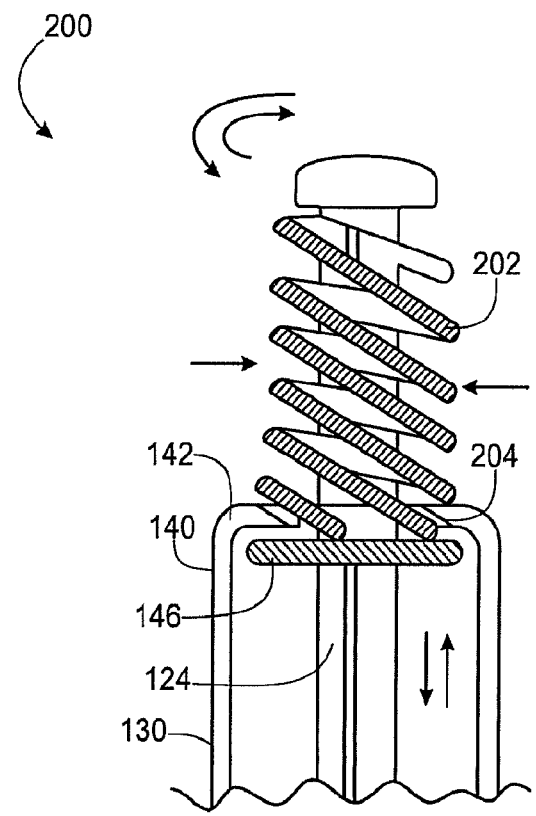
FIG. 21 is a schematic representation of an alternative, helical drive arrangement for the plunger assembly.

FIG. 21 illustrates yet another embodiment in which a helical drive assembly 200 is formed on a portion of the shaft 124 extending outwardly from the container 130. More specifically, the helical drive assembly 200 includes a helical thread 202 formed on a portion of the shaft 124 (shown here as that portion below the stop member/indicator disk). The helical thread 202 cooperates with a corresponding helical surface 204 provided on the bottom wall 142. In this manner, the outer end of the shaft 124 is selectively rotated in one direction or another to rotationally and axially advance and retract the shaft 124 in the container 130, and likewise relative to the syringe housing 102 for careful dispensing of the fluid therefrom.

Figure 22:
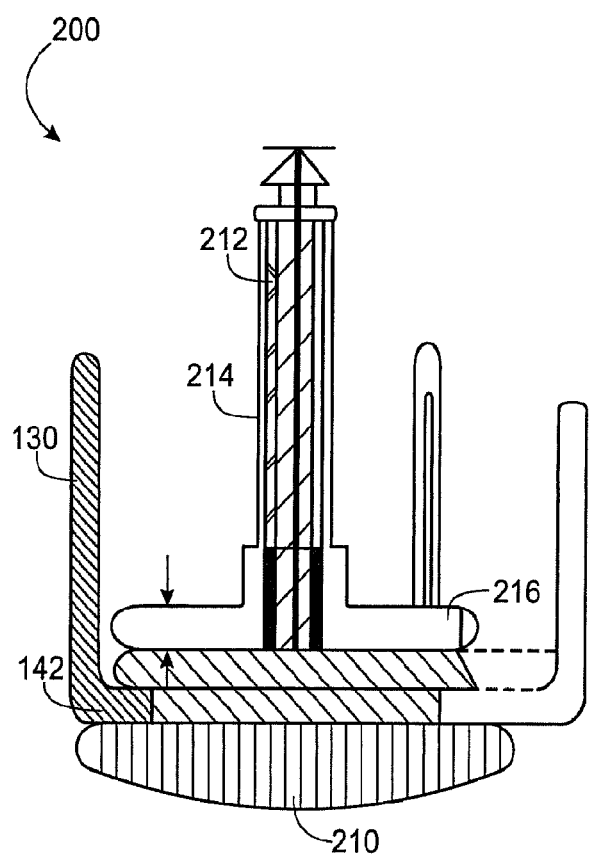
FIG. 22 illustrates another helical drive arrangement for the plunger assembly.

FIG. 22 shows a slightly different version of a helical drive assembly 200. Here, an enlarged knob 210 may be selectively rotated relative to the container. Extending axially from the knob 210 is first portion of the shaft that has an externally threaded region 212 that cooperates with a second shaft portion that has an internally threaded region 214 associated with a piston 216. In this manner, the piston 216 is selectively advanced and retracted by opposite rotation of the knob 210 relative to the container 130 to dispense fluid from the syringe assembly as desired.

Figure 23:
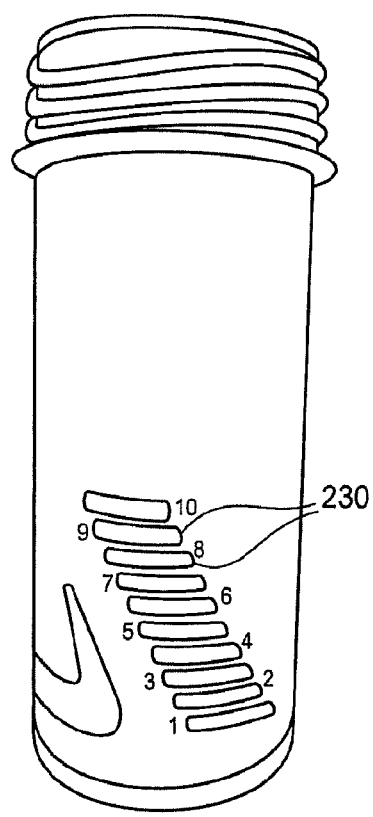
FIG. 23 shows a series of windows provided in the product packaging/label to represent the amount of fluid in the syringe assembly.

A series of indicating windows 230 are shown in FIG. 23, particularly the windows are printed on the container 130 or provided in a label received on the container. The user can thereby easily determine the amount of fluid that has been dispensed from the syringe housing by viewing the location of the indicating disk through one or more of the windows 230.

Figure 24:
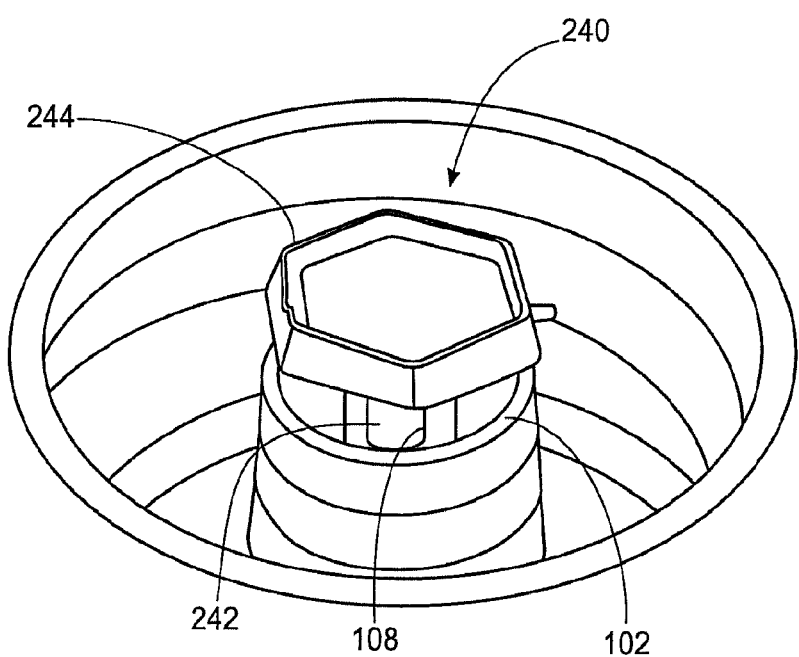
FIG. 24 is a perspective view of a closure member installed on the syringe dispensing opening.
Figure 25:
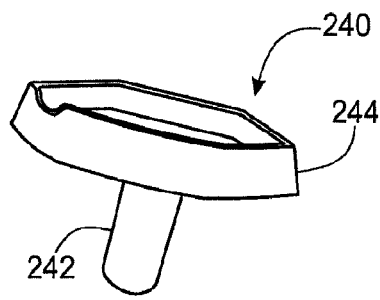
FIG. 25 is a perspective view of the closure member of FIG. 24.
Figure 26:
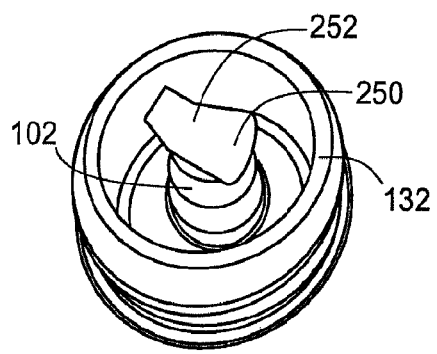
FIG. 26 is a perspective view of a tamper evident seal arrangement for the syringe dispensing opening.

Rather than using the internal surface of the cap to seal the dispensing opening 108 of the syringe housing 102, it is also contemplated that a removable plug/seal 240 may be received in the opening (FIGS. 24-25). More specifically, the plug seal 240 includes a protruding portion 242 dimensioned for a sealing, friction fit with the inner diameter of the opening 108 of the syringe housing 102. An enlarged head 244, shown here as a hexagonal-shaped head is joined to the protruding portion 242 to allow the plug/seal 240 to be manually inserted and removed from the opening 108.

Still another manner of sealing the opening 108 in the syringe housing 102 is through a foil seal 250. The foil seal 250 is heated and seals about the perimeter of the opening 108 in a manner well known in the art. A flap 252 of the seal 250 extends outwardly from the perimeter of the opening and may be easily grasped by a user to remove the tamper evident foil seal.

Another advantage of the present disclosure is that the larger container 130 is easier to grasp by a user. The extended shaft version (FIGS. 1-10) of the plunger assembly 120 can be pushed with the thumb while holding the container 130 in hand. The non-extended shaft plunger version 100' of FIGS. 11-17 easily sits upright on a countertop or planar surface, because the shaft 124' does not extend outwardly from the bottom wall 142' at the second end 138 of the container 130' and instead is flush with the bottom of the container when fully extended from the syringe housing.

The embodiments shown and described herein are easier to fill than prior art arrangements. The stop assembly provided by the stop member 146/146' abutting against the bottom wall 142/142' of the container 130/130' acts as a positive stop for filling purposes. Alternatively, if single use only is desired, once the plunger 120' (piston 122') is pushed forward, the syringe housing cavity cannot be easily refilled or retracted in the embodiment of FIGS. 11-17. Other materials or substances cannot be added to dilute virgin material originally filled in the syringe.

The enlarged container 130 provides an increased surface or label area (e.g., approximately 2" tall by 3" long) that allows for more text to be provided on the container.

A shrink band can easily be included and received over the large child resistant cap 134. An upper, annular ring on the container 130 would allow for a shrink band (not shown) to stay in place for visual tamper protection of the assembly 100. With this design, the syringe and particularly removal of the cap can only be used by removing/breaking the shrink band.

The syringe housing can be molded in opaque material so that contents stored in the cavity do not show, even though stop member/indicator disk 146 can be viewed from the outer clear/transparent container 130 with ease.

The heavy duty construction of the assembly can be useful for dangerous or expensive liquids or powders.

This written description uses examples to describe the disclosure, including the best mode, and also to enable any person skilled in the art to make and use the disclosure. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Moreover, this disclosure is intended to seek protection for a combination of components and/or steps and a combination of claims as originally presented for examination, as well as seek potential protection for other combinations of components and/or steps and combinations of claims during prosecution.

It is claimed:

1. A syringe assembly comprising:
    a housing having a cavity for receiving an associated fluid therein and having a dispensing opening communicating with the cavity through which the associated fluid is selectively dispensed;
    a plunger assembly operatively connected to the housing and including a piston and a shaft connected to the piston for selectively dispensing the associated fluid from the housing dispensing opening; and
    a container that receives the housing and plunger assembly, the container having a first opening at a first end that selectively receives a removable cap thereon and covers the dispensing opening when the cap is secured to the container and allowing access to the dispensing opening when the cap is removed from the container, and second opening at a second end that opens to the plunger assembly shaft, wherein the shaft is dimensioned so that the shaft does not extend through the container second opening, wherein the shaft includes a stop member that selectively engages a surface of the container adjacent the second opening to limit movement of the shaft through the container second opening.

2. The syringe assembly of claim 1 wherein the stop member selectively engages the container adjacent the second opening to limit movement of the shaft through the second opening.

3. The syringe assembly of claim 1 further comprising a helical drive assembly operatively associated with the shaft for advancing and retracting the shaft relative to the housing.

4. The syringe assembly of claim 3 wherein the helical drive assembly includes a helical thread on a portion of the shaft that cooperates with a corresponding helical surface on the container to rotationally and axially advance and retract the shaft relative to the housing.

5. The syringe assembly of claim 3 wherein the helical drive assembly includes cooperating first and second shaft portions that each include a helical thread region such that rotation of the first shaft portion results in advancement of the second shaft portion relative to the housing for selectively dispensing the associated fluid.

6. The syringe assembly of claim 1 further comprising a seal for selectively closing the dispensing opening.

7. The syringe assembly of claim 6 wherein the seal is a foil member that is received over the dispensing opening.

8. The syringe assembly of claim 6 wherein the seal has a protrusion dimensioned for frictional engagement with the dispensing opening.

9. The syringe assembly of claim 6 wherein the dispensing opening is located at the first end of the container for sealing engagement with an underside of the cap when the cap is secured to the container.

10. The syringe assembly of claim 1 further comprising a storage compartment in the container for selectively storing associated tools therein.

11. The syringe assembly of claim 1 further comprising a disk-shaped topical applicator mounted to the container that communicates with the dispensing opening.

12. A syringe assembly comprising:
    a housing having a cavity for receiving an associated fluid therein and having a dispensing opening communicating with the cavity through which the associated fluid is selectively dispensed;
    a plunger assembly operatively connected to the housing and including a piston and a shaft connected to the piston for selectively dispensing the associated fluid from the housing dispensing opening; and
    a container that receives the housing and plunger assembly, the container having a first opening at a first end that selectively receives a removable cap thereon and covers the dispensing opening when the cap is secured to the container and allowing access to the dispensing opening when the cap is removed from the container, and second opening at a second end that opens to the plunger assembly shaft, wherein the shaft is dimensioned so that the shaft does not extend through the container second opening, wherein the shaft includes an indicator member that is visible through the container to represent an amount of the associated fluid used or remaining in the housing cavity.

13. The syringe assembly of claim 12 further comprising indicia on the container that are adjacent the indicator member.

14. The syringe assembly of claim 12 further including windows on the container or a label provided on the container that are adjacent the indicator member.

\* \* \* \* \*